(12) United States Patent
Zhang et al.

(10) Patent No.: US 7,579,462 B2
(45) Date of Patent: Aug. 25, 2009

(54) PROCESS FOR PREPARING 17-ALLYL AMINO GELDANAMYCIN (17-AAG) AND OTHER ANSAMYCINS

(75) Inventors: Lin Zhang, San Diego, CA (US); Marcus F. Boehm, San Diego, CA (US); Siead Zegar, Orland Park, IL (US)

(73) Assignee: Conforma Therapeutics Corporation, San Diego, CA (US)

( * ) Notice: Subject to any disclaimer, the term of this patent is extended or adjusted under 35 U.S.C. 154(b) by 417 days.

(21) Appl. No.: 10/490,785

(22) PCT Filed: Sep. 18, 2002

(86) PCT No.: PCT/US02/29715

§ 371 (c)(1), (2), (4) Date: Mar. 21, 2005

(87) PCT Pub. No.: WO03/026571

PCT Pub. Date: Apr. 3, 2003

(65) Prior Publication Data

US 2005/0176695 A1    Aug. 11, 2005

Related U.S. Application Data

(60) Provisional application No. 60/326,639, filed on Sep. 24, 2001, provisional application No. 60/331,893, filed on Nov. 21, 2001.

(51) Int. Cl.
C07D 225/00 (2006.01)
C07D 295/00 (2006.01)

(52) U.S. Cl. .................................................. 540/451

(58) Field of Classification Search .................. None
See application file for complete search history.

(56) References Cited

U.S. PATENT DOCUMENTS

| 3,595,955 | A | * | 7/1971 | De Boer et al. | 424/121 |
| 4,261,989 | A | * | 4/1981 | Sasaki et al. | 424/244 |
| 5,387,584 | A | | 2/1995 | Schnur | |
| 5,883,236 | A | * | 3/1999 | Hengeveld et al. | 536/7.2 |
| 5,932,566 | A | * | 8/1999 | Schnur et al. | 514/183 |

FOREIGN PATENT DOCUMENTS

| EP | 1435939 B1 | 2/2008 |
| EP | 1923061 A1 | 5/2008 |
| WO | WO 93/14215 | 7/1993 |
| WO | WO 95/01342 | 1/1995 |
| WO | WO 00/61578 | 4/2000 |
| WO | WO 03/026571 A2 | 4/2003 |

OTHER PUBLICATIONS

Gibson et al. Atherosclerosis, 1995, 112, 47-57.*
Suchland et al. Antimicrobial Agents and Chemotherapy, 2005, 1120-1126.*
March, J. Advanced Organic Chemistry, 1992, p. 359, table 10.12.*
Buchner, J., 1999 TIBS, 24:136-141.
Caplan, A., 1999, Trends in Cell Biol., 9:262-68.
Dai, K. et al., 1996, J. Biol. Chem. 271:22030-4.
Erlichman, et al., Proc. AACR (2001), 42 abstract 4474.
Federal Register, 66(129): 35443-35444.
Grenert, J.P. et al., 1997, J. Biol. Chem., 272:23843-50.
Hartmann, F., et al., 1997, Int. J. Cancer 70:221-9.
Miller, P., et al., 1994, Cancer Res. 54:2724-2730.
Mimnaugh, E.G., et al., 1996, J. Biol. Chem. 271:22796-801.
Muise-Helmericks, R.C., et al., 1998, J. Biol. Chem. 273:29864-72.
Panaretou, B. et al., 1998, EMBO J. 17:4829-36.
Prodromou, C. et al., 1997, Cell, 90:65-75.
Progress in the Chemistry of Organic Natural Products, Chemistry of the Ansamycin Antibiotics, 33 1976, p. 278.
Scheibel, T.H., et al., 1999, Proc. Natl. Acad. Sci USA, 96:1297-302.
Schneider, C.L., et al., Proc. Natl. Acad. Sci. USA, 93:14536-41.
Schulte, T.W., et al., 1995, J. Biol. Chem.270:24585-8.
Schulte, T. W., et al., 1997, Biochem. Biophys. Res. Commun. 239:655-9.
Schnur, R., et al., 1995, J. Med. Chem. 38:3806-3812.
Segnitz, B., and Gehring, U., 1997, J. Biol. Chem. 272:18694-18701.
Sepp-Lorenzino, L., et al., 1995, J. Biol. Chem. 270:16580-16587.
Smith, D.F., et al., 1995, Mol. Cell. Biol. 15:6804-12.
Stepanova, L. et al. 1996, Genes Dev. 10:1491-502.
Stebbins, C. et al., 1997, Cell, 89:239-250.
Vasilevskaya, A., et al., 1999, Cancer Res., 59:3935-40.
Whitesell, L., et al., 1994, Proc. Natl. Acad. Sci. USA 91:8324-8328.
Caira "Crystalline Polymorphism of Organic Compounds," Topics in Current Chemistry, 198: 163-208 (1998).
International Search Report mailed May 1, 2003, for International Patent App. No. PCT/US02/29715, filed Sep. 18, 2002 (2 pages).
International Preliminary Examination Report completed Feb. 23, 2004, for International Patent App. No. PCT/US02/29715, filed Sep. 18, 2002 (3 pages).
Supplemental European Search Report mailed Nov. 12, 2004, for EP Application No. 02761732.3 (3 pages).
Supplemental European Search Report mailed Apr. 18, 2008, for EP Application No. 08101997.8 (10 pages).

* cited by examiner

*Primary Examiner*—James O Wilson
*Assistant Examiner*—Noble Jarrell
(74) *Attorney, Agent, or Firm*—Finnegan Henderson Farabow Garrett & Dunner LLP (57) ABSTRACT

Efficient chemical processes for preparing high yields, purities, and different polymorphic forms of 17-allyl amino geldanamycin (17-AAG) and other ansamycins are described and claimed.

6 Claims, 2 Drawing Sheets

PROCESS FOR PREPARING 17-ALLYL AMINO GELDANAMYCIN (17-AAG) AND OTHER ANSAMYCINS

RELATED APPLICATIONS

This is a § 371 national application of, and claims priority to, International Application Ser. No. PCT/US02/29715, filed Sep. 18, 2002, which in turn claims priority to each of U.S. Provisional Patent Application Ser. No. 60/326,639, filed Sep. 24, 2001, and U.S. Provisional Patent Application Ser. No. 60/331,893, filed Nov. 21, 2001. Each of these applications is entitled "PROCESS FOR PREPARING 17-ALLYL AMINO GELDANAMYCIN (17-AAG) AND OTHER ANSAMYCINS" and is incorporated by reference herein in its entirety, including all drawings and figures.

FIELD OF INVENTION

The invention relates to preparatory chemistry as applied to ansamycins, compounds that are useful, e.g., as antibiotics and in the treatment of various proliferative diseases, e.g., cancer.

BACKGROUND

The following description includes information that may be useful in understanding the present invention. It is not an admission that any of the information provided herein is prior art or relevant to the presently claimed inventions, or that any publication specifically or implicitly referenced is prior art.

17-allylamino-geldanamycin (17-AAG) is a synthetic analog of geldanamycin (GDM). Both molecules belong to a broad class of antibiotic molecules known as ansamycins. GDM, as first isolated from the microorganism *Streptomyces hygroscopicus*, was originally identified as a potent inhibitor of certain kinases, and was later shown to act by stimulating kinase degradation, specifically by targeting "molecular chaperones," e.g., heat shock protein 90s (HSP90s). Subsequently, various other ansamyins have demonstrated more or less such activity, with 17-AAG being among the most promising and the subject of intensive clinical studies currently being conducted by the National Cancer Institute (NCI). See, e.g. Federal Register, 66(129): 35443-35444; Erlichman et al., Proc. AACR (2001), 42, abstract 4474.

HSP90s are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J., 1999, *TIBS,* 24: 136-141; Stepanova, L. et al., 1996, *Genes Dev.* 10: 1491-502; Dai, K. et al., 1996, *J. Biol. Chem.* 271: 22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see, e.g., Caplan, A., 1999, *Trends in Cell Biol.,* 9: 262-68).

Ansamycin antibiotics, e.g., herbimycin A (HA), geldanamycin (GM), and 17-AAG are thought to exert their anticancerous effects by tight binding of the N-terminus pocket of HSP90 (Stebbins, C. et al., 1997, *Cell,* 89: 239-250). This pocket is highly conserved and has weak homology to the ATP-binding site of DNA gyrase (Stebbins, C. et al., supra; Grenert, J. P. et al, 1997, *J Biol. Chem.,* 272: 23843-50). Further, ATP and ADP have both been shown to bind this pocket with low affinity and to have weak ATPase activity (Proromou, C. et al, 1997, *Cell,* 90: 65-75, Panaretou, B. et al., 1998, *EMBO J,* 17: 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T., H. et al., 1999, *Proc. Natl. Acad. Sci. USA* 96: 1297-302; Schulte, T. W. et al., 1995, *J. Biol. Chem.* 270: 24585-8; Whitesell, L., et al., 1994, *Proc. Natl. Acad. Sci. USA* 91: 8324-8328). Ansamycins have also been demonstrated to inhibit the ATP-dependent release of chaperone-associated protein substrates (Schneider, C., L. et al., 1996, *Proc. Natl. Acad. Sci. USA,* 93: 14536-41; Sepp-Lorenzino et al., 1995, *J. Biol. Chem.* 270: 16580-16587). In either event, the substrates are degraded by a ubiquitin-dependent process in the proteasome (Schneider, C., L., supra; Sepp-Lorenzino, L., et al., 1995, *J. Biol. Chem.,* 270: 16580-16587; Whitesell, L. et al., 1994, *Proc. Natl. Acad. Sci. USA,* 91: 8324-8328).

This substrate destabilization occurs in tumor and non-transformed cells alike and has been shown to be especially effective on a subset of signaling regulators, e.g., Raf (Schulte, T. W. et al., 1997, *Biochem. Biophys. Res. Commun.* 239: 655-9; Schulte, T. W., et al., 1995, *J. Biol. Chem.* 270: 24585-8), nuclear steroid receptors (Segnitz, B., and U. Gehring. 1997, *J. Biol. Chem.* 272: 18694-18701; Smith, D. F. et al., 1995, *Mol. Cell. Biol.* 15: 6804-12), v-src (Whitesell, L., et al., 1994, *Proc. Natl. Acad. Sci. USA* 91: 8324-8328) and certain transmembrane tyrosine kinases (Sepp-Lorenzino, L. et al., 1995, *J. Biol. Chem.* 270: 16580-16587) such as EGF receptor (EGFR) and Her2/Neu (Hartmann, F., et al., 1997, *Int. J. Cancer* 70: 221-9; Miller, P. et al., 1994, *Cancer Res.* 54: 2724-2730; Mimnaugh, E. G., et al., 1996, *J. Biol. Chem.* 271: 22796-801; Schnur, R et al., 1995, *J. Med. Chem.* 38: 3806-3812), CDK4, and mutant p53. Erlichman et al., Proc. AACR (2001), 42, abstract 4474. The ansamycin-induced loss of these proteins leads to the selective disruption of certain regulatory pathways and results in growth arrest at specific phases of the cell cycle (Muise-Heimericks, R. C. et al., 1998, *J. Biol. Chem.* 273: 29864-72), and apoptsosis, and/or differentiation of cells so treated (Vasilevskaya, A. et al., 1999, *Cancer Res.,* 59: 3935-40).

Ansamycins thus hold great promise for the treatment and/or prevention of many types of cancers and proliferative disorders. However, at present the various known methods of producing ansamycins exhibit one or more of low yield, low purity, instability, environmental toxicity associated with the use of halogenated organic solvents, and additional attendant costs in terms of time, expense, waste disposal, and health risks to those taking the drugs so made. Examples of known methods include Sasaki et al, U.S. Pat. No. 4,261,989, assigned to Kaken Chemical Co, Ltd., which reports the synthesis of various ansamycin derivatives, including 17-AAG, using various organic solvents and tedious extraction techniques, and Schnur et al, U.S. Pat. No. 5,932,566 and PCT/IB94/00160 (WO 95/01342), assigned to Pfizer Inc., which describe similar processes.

It is an object of the invention to improve one or more of the shortcomings of the existing art, i.e., ameliorate one or more of low yield, low purity, instability, environmental toxicity associated with the use of halogenated organic solvents, and additional attendant costs in terms of time, expense, waste disposal, and health risks.

SUMMARY OF THE INVENTION

There are several inventive aspects. In a first aspect, the invention features an efficient chemical process for preparing ansamycins that employs the use of both volatile aprotic and volatile protic solvents. The process is useful, inter alia, for preparing benzoquinone geldanamycin derivatives, e.g., 17-AAG or its 4,5-dihydro analog, from benzoquinone geldanamycins (GDM). One embodiment of the latter aspect combines, e.g., 4,5-dihydro geldanamycin or geldanamycin (or other benzoquinone geldanamycins having reactive moieties, e.g., a methoxy, on the benzoquinone portion), and a nucleophile in a volatile aprotic solvent, e.g., a member selected from Table 1, to produce a crude product which is then concentrated by the use of evaporation, and to the resulting product added a volatile protic solvent, either as a wash or under conditions suitable to crystallize or precipitate the ansamycin product out of solution. In either event, both solvent types are conveniently removed, e.g., by filtration, centrifugation, decanting and/or evaporation. The benefits, depending on the specific embodiment, include but are not limited to reduced purification work-up, increased yield and/or purity, and the use of clinically acceptable reagents.

Following is an exemplary reaction scheme for one aspect and embodiment of the invention:

$R^1$ and $R^2$ are either both hydrogen, in which case the bond between C4 and C5 is a single bond, or else $R^1$ and $R^2$ are both non-existent, in which case there is a double bond between C4 and C5. The dashed line between C4 and C5 denotes both possibilities. Nu—H is a nucleophile that replaces the $R^3$O— group at position 17 during the reaction. $R^3$ is preferably an alkoxy of 1-4 carbons, preferably methoxy. The reaction takes place in a volatile aprotic solvent, e.g., one selected from the following possibilities: THF, ethyl-ether, MTBE, THP, dioxane, ethyl sec-butyl ether, methyl butyl ether, ethyl acetate, or methyl acetate, and results in a crude, substituted product. Non-halogenated solvents are preferred. In some embodiments, the nucleophile is slowly added to the to-be-substituted benzoquinone geldanamycin derivative such that predominantly singly-substituted product is produced. This step may optionally be monitored using, e.g., a chromatographic technique, e.g., TLC, HPLC, or other such procedure commonly known in the art, e.g., spectrophotometry, NMR, etc., to gauge reaction completion. Such techniques may also be used at subsequent steps in the process, e.g., those described below. In preferred embodiments, the reaction is allowed to continue to completion such that substantially all benzoquinone ansamycin reactant is converted to its corresponding derivative.

Following the preparation of crude substituted product in volatile aprotic solvent, the product is concentrated using evaporation and then slurred with or dissolved in a volatile protic solvent, e.g., isopropanol, ethanol and/or water. The term "slurried" as used herein denotes suspension of a solid in a liquid under conditions in which the solid, e.g., ansamycin, does not dissolve appreciably. In such manner a "wash" may be effected, especially if impurities exhibit greater solubility under such conditions than does the solid. Example 1, below, is illustrative. An alternative or conjunctive to a wash is a crystallization procedure, e.g., as embodied in example 2, below.

Each of the volatile aprotic and protic solvents may be conveniently eliminated, e.g., by evaporation, which itself may be in combination with centrifugation, heat and/or vacuum. As one of ordinary skill will appreciate, lower temperatures may also be used provided the pressure is coordinately lessened (increased vacuum). Heat or standard room temperature drying may be used alone in some embodiments. One or more filtering steps may also be employed, and washes across the filter(s) using the volatile protic solvent(s) may be conveniently used to reduce impurities.

In some embodiments, nucleophiles are used and selected from the group consisting of amines, thiols, thiolates, thioether, alcohols, and alkoxides, each of which constitutes, possesses, or may be modified to possess one or more functional groups to which additional chemical moieties may later be attached, e.g., to tether the resulting benzoquinone ansamycin derivative to another structure. In some preferred embodiments, the nucleophile is a primary or secondary amine having structure:

wherein $R^4$ and $R^5$ independently represent hydrogen, $(C_1-C_{12})$alkyl or $(C_1-C_{12})$ alkyl optionally substituted with allyl, propargyl, hydroxy, amino, mercapto, carboxylato, or halogen functional groups. A nonexhaustive list of amines in general that can be used includes those found in Table I of U.S. Pat. No. 4,261,989, issued to Sasaki. It will be appreciated that other functional groups such as olefins may also be attached. In some embodiments, e.g., as in the production of 17-AAG or the 4,5 dihydro analog, the nucleophile is allyl amine. Other useful nucleophiles that can be used include but are not limited to those appearing in the detailed description section.

In some embodiments, it may be useful to use reduced lighting in one or more of the steps of the process to prevent or minimize photodegradation of products and/or reactants. To this end, the final product may also be stored in a light-resistant container to preserve or assist in product stability and shelf life.

The foregoing process aspect of the invention can feature any combination of embodiments stated that are consistent with each other. In a broader process aspect, the invention features methods of concentrating and/or purifying ansamycins. The methods utilize volatile aprotic solvents, preferably nonhalogenated solvents, following by evaporation and washes or crystallization using a volatile protic solvent such as those used in Examples 1 and 2, below. Other aspects of the invention feature the products made by such processes, and each product can be made according to any of the foregoing mentioned process embodiments.

In another aspect, the invention features a method of preparing 17-AAG comprising providing 17-AAG dissolved in a protic solvent solution and crystallizing said 17-AAG from said protic solvent solution, said protic solvent solution substantially free of water, and then removing said protic solvent solution. The term "preparing" means, e.g., concentrating, purifying, or converting an existing polymorphic form of 17-AAG into another form of 17-AAG. When this term is followed by the transitional phrase "comprising," it may also include additional later steps such as dissolving in a solution, creating a formulation, etc. The term "removing" does not necessarily imply complete removal, but preferably substantial removal such that predominantly solid 17-AAG is left after that step, with minor fractions of solvent optionally present. In one embodiment, the protic solvent is isopropanol and the 17-AAG after crystallizing from and removing the isopropanol exhibits a melting point of about 146° C.-153° C. or about 155° C. or less. A related though different aspect entails formation of a higher melting point polymorph of 17-AAG, preferably one that exhibits a melting point in the range of about 200° C. or more. In some preferred embodiments, the melting point is about 206-212° C. This can be accomplished by crystallization in a protic solvent solution, e.g., ethanol, that may or may not contain water. Applicants have observed that the presence of water in the solvent usually increases the ultimate melting temperature of the resulting 17-AAG polymorph. The compounds created by the foregoing methods are also claimed, with or without one or more other agents ultimately mixed in. Optionally, such compositions are packaged in a light-resistant container to prevent, minimize, or retard degradation. It is anticipated that other lipophillic compounds will similarly give rise different melting-point polymorphs. These polymorphs feature or are likely to feature different utilities, e.g., the lower melting-point forms are more easily dissolved and formulated, and the higher melting point forms are anticipated to exhibit longer stability.

In another aspect, the invention features a method of converting a first polymorphic form of an ansamycin to a second polymorphic form of an ansamyin comprising dissolving an ansamycin of a first polymorphic form in a protic solvent solution under conditions sufficient to yield a second polymorphic form of ansamycin. A high melting point type can be converted to a low melting point form and vice-versa. The ansamycin is preferably 17-AAG, but the technique is anticipated to have utility for other lipophilic compounds as well and evidence for this is shown in Examples 1-5. Potential embodiments for this aspect can track features of the preceding aspect embodiments.

Advantages realized by the invention, depending on precise aspect and embodiment, include one or more of high yield, high purity, stability, reduced environmental and patient toxicity, and additional attendant reductions in time, expense, ease of formulation, and waste storage and disposal. Other advantages, aspects, and embodiments will be apparent from the figures, the detailed description, and claims to follow.

DETAILED DESCRIPTION OF THE INVENTION

Figure 1:
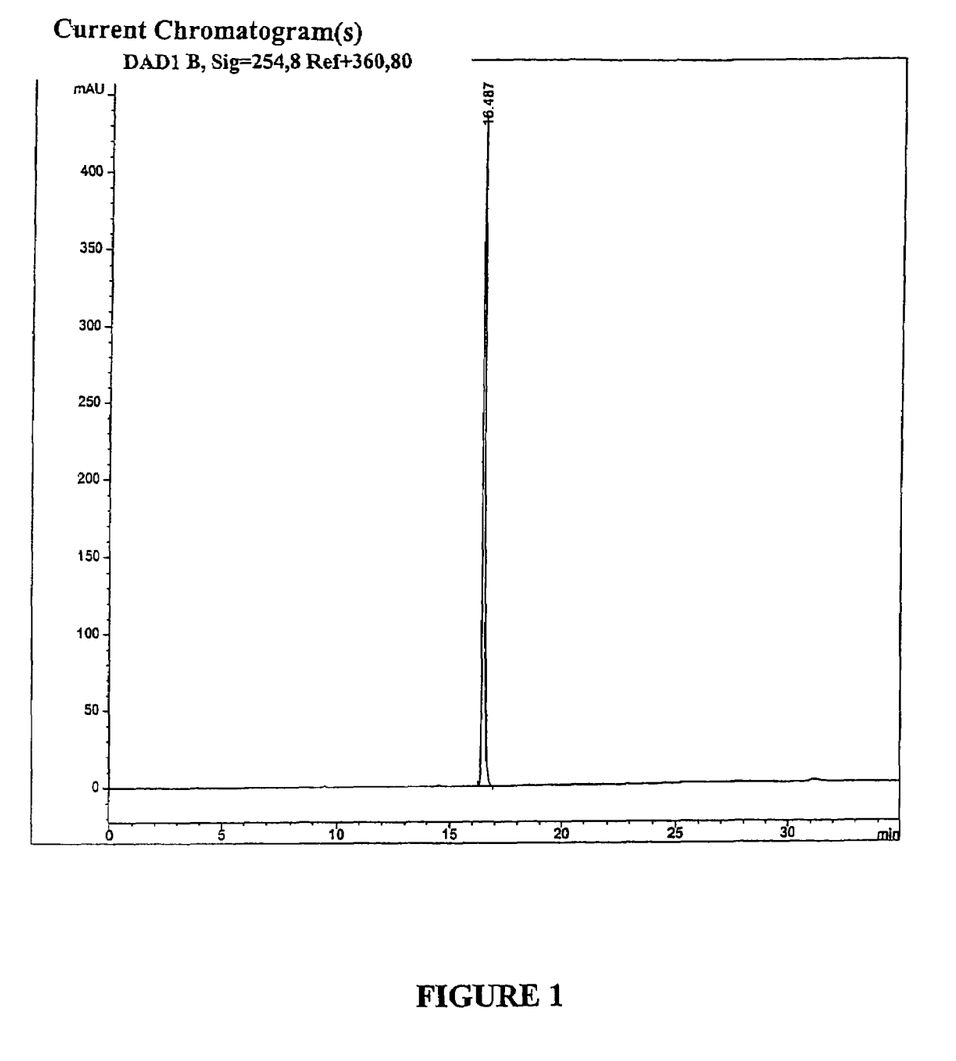
FIG. 1 is an HPLC chromatogram of 17-allylaminogeldanamycin obtained using a Zorbax 300 SB-C8 (250 cm×4.6 mm, 5 μ) column, Mobile phase: Acetonitrile (0.05% TFA): water (0.05% TFA); 30:70; flow-rate: 1 mL/min detected at 254 nm; the retention time for the peak shown appears at 16.49 min.
Figure 2:
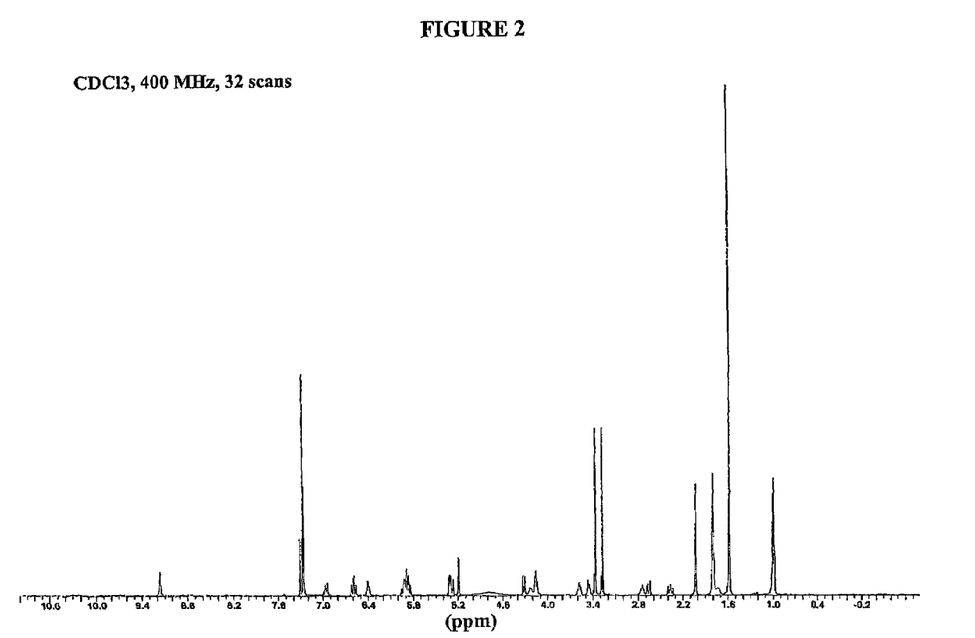
FIG. 2 shows a $^1$H NMR (400 MHz, CDCl$_3$) spectrum. The chemical shift and multiplicities are consistent with the formation of the desired product.

The invention relates to improved processes for preparing ansamycins, e.g., benzoquinone ansamycins and derivatives thereof, e.g., 17-AGG and its 4,5 dihydro analog. The processes avoid time-consuming and expensive work-ups associated with extractions and preparative chromatographic separations, while affording good purity and yield.

In some aspects and embodiments, the technique includes nucleophilic attack in one or more volatile aprotic solvents, e.g., an ether or acetate, preferably nonhalogenated, and under conditions suitable for dissolving both reactants and product(s). The resulting product(s) is/are then concentrated by evaporation, and to the concentrated product added a volatile protic solvent, e.g., a volatile alcohol and/or water, under conditions in which the volatile protic solvent either serves the purpose of a wash or a (re)crystallization media Filtration, centrifugation, decanting, and/or evaporation may be used to aid either procedure. The resulting product(s) can be used directly or indirectly for a utility associated with ansamycins, e.g., as antibiotics or anti-cancer agents. In terms of indirect utility, the product(s) is/are useful, e.g., as an intermediate(s) in the synthesis of yet further ansamycin derivatives, e.g., those described in U.S. Pat. No. 5,932,566 and PCT/IB94/00160 (WO 95/01342), issued to Schnur et al, and assigned to Pfizer Inc.

Prior to the invention, DMF, DMSO, $CH_2Cl_2$, and $CHCl_3$ were the mediums of choice for preparing ansamycins and performing substitutions and nucleophilic additions thereto. These reagents and processes require laborious work-ups and multiple water washes and EtOAc extractions. The use of chlorinated solvents in particular is discouraged in today's regulatory climate. Chlorinated solvents are not environmentally friendly and residual exposure poses a potential health risk. Moreover, Applicants have found that such solvents promote degradation products that compromise purity and yield. The inventive process is much more direct, the products formed typically in greater yields and greater purity, and environmental and health issues avoided or minimized, thus lending well to commercial applications.

The term "optionally" as used in the claims indicates that performance of the step immediately following that term is not necessary to fulfillment of the claim.

The terms "removing" and "concentrating" do not necessarily imply 100% elimination of solvent, and may entail lesser percentages of removal or concentration.

The term "nonhalogenated" means not containing one or more halogen atoms, e.g., F, Cl, Br, and I. An illustrative halogenated solvent includes $CHCl_3$ (chloroform).

By "wash" denotes that the protic solvent, under the conditions employed, does not appreciably dissolve ansamycins. A wash may include the creation of a slurry and in any event has the effect of removing impurities.

By "volatile aprotic solvent" is meant one with a boiling point of between about 35 and 102° C. Preferred are those aprotic solvents shown in Table I, below. Aprotic solvents are considered to be "non-structured", i.e., lacking an extensive network of hydrogen bonds in the pure liquid state. However, certain aprotic solvents have the capability of dissolving and stabilizing compounds or solutes themselves protic, for examples alcohols or water itself. Water and THF for example are miscible. In general, aprotic solvents lack the ability to self-dissociate into ions under ordinary circumstances.

By "volatile protic solvent" includes, e.g., isopropanol, ethanol, water, and mixtures thereof Water is a classical protic solvent. Liquid phase water is characterized by an extensive network of hydrogen bonds. In the liquid phase, each individual water molecule forms four hydrogen bonds to neighboring water molecules. Disruption of this extensive hydrogen bond network entails a significant input of energy and this energy cost is reflected in the relatively high boiling point (100° C.) for a low molecular weight compound. Alcohols, especially low molecular weight alcohols (those having few than 12 carbon atoms), exhibit similar properties to water. In the liquid state, a hydrogen bonded network is established. Alcohols differ, however, in the number of hydrogen bonds established: only three hydrogen bonds occur between alcohol solvent molecules whereas four such bonds are typically present in liquid water. This in effect translates into a greater "looseness" between alcohol solvent molecules, manifesting as lower boiling points and freezing temperatures relative to water. One physical property of water/alcohol mixtures is the formation of azeotropic mixtures. The addition of an alcohol to water causes a decrease in the boiling point of water. The following table illustrates that the addition of 10% ethanol to water will produce a solvent which is more volatile than water itself.

TABLE I

| wt-% ethanol | freezing point (° C.) | boiling point (° C.) |
|---|---|---|
| 0 | 0 | 100 |
| 10 | −4.5 | 91.45 |
| 20 | −10.7 | 87.15 |
| 40 | −27.0 | 83.1 |
| 50 | −37.0 | 81.90 |
| 60 | 45.0 | 81.0 |
| 70 | 53.0 | 80.20 |
| 80 | 64.5 | 79.35 |
| 90 | −109 | 78.5 |
| 92.4 | −123 | 78.24 |
| 95.57 | −119.3 | 78.15 |
| 100 | −114.5 | 78.3 |

Table I further illustrates that mixtures which are largely ethanol, e.g., approximately 95% ethanol, 5% water, boil at the same temperature as pure ethanol. For this reason, it is in practice impossible to obtain pure ethanol by distilling water/ethanol mixtures, a fact well known in the art of distilling spirits. Another characteristic of protic solvents is their tendency to undergo self ionization to some extent. Water for example dissociates into oppositely charged ions according to the following equation:

$2H_2O \leftrightarrows H_3O^+ + {}^-OH$

Pure water itself dissociates to a small but measurable extent and this leads to the well-known value of $[H_3O^+]=10^{-7}$ (or pH 7) for pure water at 25° C.

A "non-oxidizing environment" does not mean that no oxidation is possible or actually occurs, simply that such possibility is reduced. Examples include but are not limited to using reduced lighting and/or reduced gaseous oxygen. The latter occurs, e.g., if air or oxygen is replaced with nitrogen and/or argon gas.

Ansamycins and Benzoquinone Ansamycins

The term "ansamycin" is well-known in the art and refers to a broad class of structures characterized by aliphatic rings of various length and composition bridging opposite ends of aromatic ring structures and their reduced equivalents. Subsumed within this broad class is the sub-class, benzoquinone ansamycins. Illustrative species include:

A "benzoquinone ansamycinin" as used herein possesses a benzoquinone moiety and includes any benzoquinone ansamycinin known in the art. In some aspects featuring nucleophilic addition, these preferably include an alkoxy moiety on the benzoquinone portion of the molecule, preferably a methoxy, and preferably at the 17 position, that can be replaced by a nucleophile. The result of the reaction is the formation of a "benzoquinone ansamycin derivative." Ansamycins and benzoquinone ansamycins according to the invention may be synthetic, naturally-occurring, or a combination of the two, i.e., "semi-synthetic." They may also be monomeric or dimeric. Illustrative examples of dimeric ansamycins include but are not limited to those found in Rosen et al., International Application PCT U.S. 00/09512 (WO 00/61578), filed Apr. 7, 2000 and published Oct. 19, 2000. Other exemplary benzoquinone ansamycins useful in the processes of the invention and their methods of preparation include but are not limited to those described, e.g., in U.S. Pat. No. 3,595,955 (describing the preparation of geldanamycin), U.S. Pat. Nos. 4,261,989, 5,387,584, and 5,932,566. Geldanamycin is also commercially available, e.g., from CN Biosciences, an Affiliate of Merck KGaA, Darmstadt, Germany, and headquartered in San Diego, Calif., USA (cat. no. 345805. The biochemical purification of 4,5-Dihydrogeldanamycin and its hydroquinone from cultures of *Streptomyces hygroscopicus* (ATCC 55256) are described in International Application Number PCT/US92/10189, assigned to Pfizer Inc., published as WO 93/14215 on Jul. 22, 1993, and listing Cullen et al. as inventors; an alternative method of synthesis for 4,5-Dihydrogeldanamycin by catalytic hydrogenation of geldanamycin is also known. See e.g., Progress in the Chemistry of Organic Natural Products, *Chemistry of the Ansamycin Antibiotics,* 33 1976, p. 278.

Nucleophiles

Many types of nucleophiles exist that can be used in the inventive processes described herein. Preferred are those selected from the group consisting of thiols, thiolates, thioether, alcohols, and alkoxides, each of which constitutes, possesses, or may be modified to possess, one or more functional groups to which additional chemical moieties may later be attached, e.g., antibodies. In some preferred embodiments, the nucleophile is a primary or secondary amine having structure:

wherein $R^4$ and $R^5$ independently represent hydrogen, ($C_1$-$C_{12}$)alkyl or ($C_1$-$C_{12}$) alkyl optionally substituted with allyl, propargyl, hydroxy, amino, mercapto, carboxylato, or halogen functional groups. A nonexhaustive list of amines in general that can be used include those found in Table I of U.S. Pat. No. 4,261,989, issued to Sasaki. It will be appreciated that other functional groups such as olefins may also be attached. In some embodiments, e.g., as in the production of 17-AAG or the 4,5 dihydro analog, the nucleophile is allyl amine. Allyl amine and other nucleophiles described herein are available commercially, e.g., from Sigma-Aldrich. The following Table illustrates some preferred nucleophiles that can be used in various embodiments of the invention.

TABLE II

NH2

$\diagup$NH2

$\diagup\!\!\!\diagdown$NH2

$\diagup\!\!\!\diagdown\!\!\!\diagup$NH2

$\diagup\!\!\!\diagdown\!\!\!\diagup\!\!\!\diagdown$NH2

$\diagup\!\!\!\diagdown\!\!\!\diagup\!\!\!\diagdown\!\!\!\diagup$NH2

$=\!\!\!\diagdown\!\!\!\diagup$NH2 cyclopropyl-CH2-NH2 benzyl-NH2

(pyridin-2-yl)-CH2-NH2

(pyridin-3-yl)-CH2-NH2

(pyridin-4-yl)-CH2-NH2

(thiophen-2-yl)-CH2-NH2

HO$\diagdown\!\!\!\diagup$NH2

HO$\diagup\!\!\!\diagdown\!\!\!\diagup$NH2

HO$\diagup\!\!\!\diagdown\!\!\!\diagup\!\!\!\diagdown$NH2

Geldanamycin-N$\diagup\!\!\!\diagdown\!\!\!\diagup\!\!\!\diagdown$NH2
(geldanamycin dimer)

Geldanamycin-N$\diagup\!\!\!\diagdown$O$\diagup\!\!\!\diagdown$NH2
(geldanamycin dimer)

Volatile Aprotic Solvents

Exemplary volatile aprotic solvents useful in various embodiments of the invention include those shown in Table III:

TABLE III

| Compound Name (acronym) | Structure | Boiling Point (° C.) | Source |
|---|---|---|---|
| ethyl ether | | 35 | commercially available (Sigma-Aldrich) |
| Methyl tert-butyl ether (MTBE) | | 55-56 | commercially available (Sigma-Aldrich) |
| Tetrahydrofuran (THF) | | 65 | commercially available (Sigma-Aldrich) |
| 1,4-dioxane | | 100-102 | commercially available (Sigma-Aldrich) |
| Tetrahydropyran (THP) | | 88 | commercially available (Sigma-Aldrich) |
| sec-butyl methyl ether | | 75 | commercially available (Sigma-Aldrich) |
| methyl butyl ether | | 70-71 | commercially available (Sigma-Aldrich) |
| methyl acetate | | 57-58 | commercially available (Sigma-Aldrich) |
| ethyl acetate | | 77 | commercially available (Sigma-Aldrich) |

This list is illustrative only, and those of ordinary skill in the art will recognize that other volatile aprotic solvents also exist that can be used. Ethers and acetates are particularly useful in that they are polar, aprotic media; they dissolve a variety of organic compounds, they share properties of both water and hydrocarbons, and they have alkyl "portions" and oxygen atoms with lone electron pairs.

Reaction Vessels

Suitable reaction vessels for the present invention are commercially available glass reaction flasks equipped with ground-glass joints. Typically such vessels are used with teflon or other inert material coated magnetic stirbars, e.g., coated with PTFE or other inert coating. In scaled-up industrial syntheses, many metal reaction vessels are sealable and hence innately light resistant. Mechanical stirring using stir shafts and/or paddles inserted into the reaction vessel may also be employed. For the exclusion of light, simple darkening of room light may suffice. Alternatively, the reaction flask and any portions of the reaction having light-sensitive material may be wrapped in aluminum foil or bottled or packaged in another type of light-resistant container as known in the art.

A reaction that requires a controlled rate of addition may be performed in a multi-necked, round-bottom flask equipped with an addition funnel (dropping funnel). A simple addition funnel is similar to a separatory funnel with a male standard taper joint at the outlet; permitting dropwise addition of a liquid reactant or solution, with the stopcock serving as a means to control drop rate. Teflon stopcocks are preferred for addition funnels so that the use of stopcock grease, which can be leached into organic solvents and contaminate desired products, is avoided.

In many small-scale reactions it is often convenient to make additions of liquids with a syringe allowing precise control over the volume of reagent added per unit time. Yet another way to add liquid reagent is via a syringe pump, as commonly known in the art. Adjustable flow rate pumps and apparati may also be used.

Reaction Monitoring

The claim term "monitored using a chromatographic technique" means to determine the presence and/or amount of a desired product, or, alternatively, the absence and/or amount of a reagent or undesired product. Several methods are known in the art, a few of which are discussed below.

TLC

Thin layer chromatography (TLC) is a form of adsorption chromatography in which a thin layer of adsorbent supported on a flat surface is utilized as a stationary phase. The most common adsorbents used in TLC are silica gel and alumina. Keiselguhr and cellulose are least commonly used. Elution or development of a TLC chromatogram is accomplished by capillary movement of the solvent up the thin layer of adsorbent.

The eluent used for TLC will depend on the type of adsorbent and the affinity of the compound to be analyzed for the adsorbent. TLC is very useful for monitoring the progress of reactions, in detecting intermediates in reactions, in analyzing crude products or unknown mixtures to determine the number of components, and for checking the efficiency of purification processes. For colorless organic compounds, visualization of the compound on the adsorbent may be accomplished using a number of techniques known in the art. However, in the present invention, both starting material and product are colored yellow and purple respectively and are visible to the eye.

HPLC

In High-Pressure Liquid Chromatography (HPLC), the liquid phase is forced over the stationary phase by pressure, thereby increasing the flow of eluent through a column containing adsorbent. Solvent mixtures and solvent gradients may be employed using modern commercial instruments. Variable wavelength UV detectors are typically employed for optimal detection of starting materials and products and, with suitable calibration of the signal, amounts of materials detected can be quantified using commercially available software.

Solvent Removal

It is often necessary to concentrate a solution or completely remove solvents in order to obtain a desired product from a reaction mixture, an extract, a chromatographic fraction, or from mother liquors from a (re)crystallization. This may be done by simple or fractional distillation techniques at atmospheric pressure or under reduced pressure. Sometimes atmospheric-pressure distillation is used to remove the bulk of the solvents, and remaining traces are then removed at reduced pressure. In any event, due consideration must be given to the stability and volatility of the desired product, i.e., care must be taken to avoid product decomposition due to overheating.

Commercially available rotary evaporation devices exist to accomplish solvent removal and lyophilization. Other simple devices are known to the skilled artisan. Methods of removing solvent at reduced temperatures under corresponding higher vacuum are also known to the skilled artisan.

Filtration

Filtration is the separation of insoluble solids from a liquid by use of a porous barrier known as a filter; the liquid passes through the filter while the solid is retained on the filter. The liquid can pass through the filter by force of gravity (gravity filtration) and/or by use of suction (suction filtration). The process of filtration is used to clarify a solution and/or to collect a solid. The filters used most often in organic chemistry are filter paper and sintered glass frits, both of which are commercially available from a variety of sources, and familiar to the skilled artisan. Suction filtration typically employs Buchner, Hirsch or sintered glass frits. In suction filtration, pressure is reduced below the filter by means of an aspirator or other means of vacuum; atmospheric pressure then forces the liquid through the filter.

(Re)crystallization

Crystallization is the deposition of crystals from a solution or melt of a given material. During the process of crystal formation, like molecules tend to become attached to a growing crystal composed of the same type of molecules because of a better fit in a crystal lattice for molecules of the same structure than for other molecules. If the crystallization process is allowed to occur under near-equilibrium conditions, the preference of molecules to deposit on surfaces composed of like molecules will lead to an increase in the purity of the crystalline material. Thus the process of crystallization is an important method of purification. Crystallization is subsumed under the broader term "precipitation," which indicates a dissolved compound ceasing to be dissolved, and effectively taking solid form outside of solution, whether "crystallized" or not. The precipitation or crystallization may occur over a prolonged period of time, e.g., seconds to hours or days. These processes also depend on temperature, as demonstrated in Example 2, below, and further depend on the properties of the specific solvent and solutes being used, with a solubility differential across warm versus cooler temperatures. The term "recrystallization" denotes that one or more previous crystallizations have already been performed on the compound, whether or not using the same solvent and conditions, and whether or not sufficient to achieve the same or different melting point polymorph.

Indeed, one aspect of the invention is the ability to form and exploit different polymorphic structures. Applicants have identified the possibility for multiple relatively pure forms (polymorphs) of 17-AAG, some possessing a relatively low melting point of about 147-153° C., e.g., when crystallized from substantially pure isopropanol and some characterized by a higher melting point of between about 200-212° C., e.g., when crystallized from ethanol combined with a fraction of water. The water may be premixed with the ethanol or later added to the ethanol solution already containing 17-AAG dissolved therein. The lower melting point form of 17-AAG is more readily soluble at room temperature in a variety of solvents and oils than is the higher melting point form of 17-AAG and offers potential advantages for formulating the 17-AAG as a drug or pharmaceutical composition. The higher melting point form may offer advantages of greater chemical stability under various conditions, i.e., exhibit longer shelf life under various storage conditions. Depending on the end-goal, one may readily convert one form to another simply by dissolving and crystallizing in the appropriate solvent. A similar phenomenon is observed using 17-amino geldanamycin ("17-AG"; see Examples 5,6), suggesting that different polymorphic forms are achievable for other ansamycins and, likely, other unrelated compounds as well.

EXAMPLES

Example 1

Synthesis of 17-Allyl Amino Geldanamycin (17-AAG)

To 45.0 g (80.4 mmol) of geldanamycin in 1.45 L of dry THF in a dry 2 L flask was added drop-wise over 30 minutes, 36.0 mL (470 mmol) of allyl amine in 50 mL of dry THF. The reaction mixture was stirred at room temperature under nitrogen for 4 hr at which time TLC analysis indicated the reaction was complete [(GDM: bright yellow: Rf=0.40; (5% MeOH-95% CHCl3); 17-AAG: purple: Rf=0.42 (5% MeOH-95% CHCl3)]. The solvent was removed by rotary evaporation and the crude material was slurred in 420 mL of H2O:EtOH (90:10) at 25° C., filtered and dried at 45° C. for 24 hr to give 40.9 g (66.4 mmol) of 17-AAG as purple crystals (82.6% yield, >98% pure by HPLC monitored at 254 nm). MP 206-212° C. $^1$H NMR and HPLC are consistent with the desired product.

Example 2

Crystallization of 17-AAG in Isopropanol

An alternative method of purification is to, instead of crystallizing in ethanol, dissolve the crude 17-AAG from example 1 in 800 mL of 2-propyl alcohol (isopropanol) at 80° C. or reflux (approximately 82.2° C.) and then cool to room temperature. Filtration followed by drying at 45° C. for 24 hr gives 44.6 g (72.36 mmol) of 17-AAG as purple crystals (90% yield, >99% pure by HPLC monitored at 254 nm). MP 147-153° C. $^1$H NMR and HPLC are consistent with the desired product.

Example 3

Ethanol Wash of the 17-AAG Polymorph of Example 2

An alternative method of purification is to slurry the 17-AAG product from example 2 in 400 mL of H2O:EtOH (90:10) at 25° C., filtered and dried at 45° C. for 24 hr to give 42.4 g (68.6 mmol) of 17-AAG as purple crystals (95% yield, >99% pure by HPLC monitored at 254 nm). MP 147-153° C. $^1$H NMR and HPLC are consistent with the desired product.

Example 4

Polymorph Conversion: Recrystallization of 17-AAG in Ethanol

An alternative method of purification is to dissolve the 17-AAG product from example 2 in 300 mL of EtOH at reflux (approximately 80° C.), followed by addition of 1,200 mL of H2O and cooling to room temperature. The solids were collected by filtration and dried at 45° C. for 24 br to give 41.0 g (67 mmol) of 17-AAG as purple crystals (93% yield, >99% pure by HPLC monitored at 254 nm). MP 206-212° C. $^1$H NMR and HPLC are consistent with the desired product.

Example 5

Synthesis of 17-Amino Geldanamycin (17-AG)

To 2.0 g (3.57 mmol) of geldanamycin in 40 ml of dry THF in a flame-dried flask was added 2.55 ml (17.8 mmol, solution in methanol, ca 7N) of ammonia under nitrogen. The reaction mixture was stirred at room temperature for 24 h at which time TLC analysis indicated the reaction was complete. The solvent was removed by rotary evaporation and the crude material was dissolved in 30 mL of EtOH and crystallized by addition of 120 mL of water to give 1.8 g (3.30 mmol) of 17-AG as red crystals (99% pure by HPLC). MP 284-286° C. $^1$H NMR and HPLC are consistent with the desired product.

Example 6

Recrystallization of 17-AG in Isopropanol

An alternative method of purification of 17-AG from example 5, is to dissolve the final 17-AG product in 30 mL of substantially pure 2-propyl alcohol (isopropanol) at 80° C. or reflux (approximately 82.2° C.) and then cool to room temperature. Filtration followed by drying at 45° C. for 24 hr gives 1.5 g (2.7 mmol) of 17-AAG as purple crystals (76% yield, >99% pure by HPLC monitored at 254 mm). MP 267-271° C. $^1$H NMR and HPLC are consistent with the desired product.

The foregoing examples are not limiting and are merely representative of various aspects and embodiments of the present invention. All documents cited are indicative of the levels of skill in the art to which the invention pertains. The disclosure of each document is incorporated by reference herein to the same extent as if each had been incorporated by reference in its entirety individually, although none of the documents is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

It will be readily apparent to one skilled in the art that varying substitutions and modifications may be made to the invention without departing from the scope and spirit of the invention. Thus, such additional embodiments are within the scope of the invention and the following claims.

The invention illustratively described herein suitably may be practiced in the absence of any element or elements, limitation or limitations which is not specifically disclosed herein. Thus, for example, while the terms "comprising", "consisting essentially of" and "consisting of," each carries a different meaning as a transition phrase, each such phrase may be used in lieu of the others to demonstrate a different aspect or embodiment of the invention. The terms and expressions which have been employed are used as terms of description and not of limitation, and there is no intention in the use of such terms and expressions of excluding any equivalents of the features shown and described, or portions thereof It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group, and exclusions of individual members as appropriate.

Other embodiments are within the following claims.

We claim:

1. A method of preparing 17-allylamino-geldanamycin, comprising
    providing a solution of 17-allylamino-geldanamycin in isopropanol, wherein said isopropanol is substantially free of water; and
    crystallizing said 17-allylamino-geldanamycin from said solution to provide 17-allylamino-geldanamycin having a melting point of 147° C.-153° C.

2. The method of claim 1 wherein providing said solution of 17-allylamino-geldanamycin in isopropanol comprises dissolving 17-allylamino-geldanamycin in isopropanol at 80° C. or reflux, wherein said isopropanol is substantially free of water.

3. The method of claim 2 wherein crystallizing said 17-allylamino-geldanamycin from said solution comprises cooling said solution.

4. The method of claim 1 further comprising drying said 17-allylamino-geldanamycin having a melting point of 147° C.-153° C. at 45° C.

5. The method of claim 1 further comprising
    dissolving 17-allylamino-geldanamycin having a melting point of about 147° C.-153° C. in aqueous ethanol at about 80° C. to provide a solution of 17-allylamino-geldanamycin and
    crystallizing 17-allylamino-geldanamycin from said solution to provide 17-allylamino-geldanamycin having a melting point of 206° C.-212° C.

6. The method of claim 5 further comprising drying said 17-allylamino-geldanamycin having a melting point of 206° C.-212° C. at 45° C.

* * * * *

UNITED STATES PATENT AND TRADEMARK OFFICE
CERTIFICATE OF CORRECTION

PATENT NO. : 7,579,462 B2  Page 1 of 1
APPLICATION NO. : 10/490785
DATED : August 25, 2009
INVENTOR(S) : Lin Zhang, Marcus F. Boehm and Siead Zegar

It is certified that error appears in the above-identified patent and that said Letters Patent is hereby corrected as shown below:

Column 16, line 46, delete "about".

Column 16, line 47, delete "about".

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,579,462 B2 | Page 1 of 1 |
| APPLICATION NO. | : 10/490785 | |
| DATED | : August 25, 2009 | |
| INVENTOR(S) | : Zhang et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 417 days Delete the phrase "by 417 days" and insert -- by 1076 days --

Signed and Sealed this

Thirteenth Day of April, 2010

David J. Kappos
*Director of the United States Patent and Trademark Office*